US012778136B2

(12) United States Patent
Yao et al.

(10) Patent No.: US 12,778,136 B2
(45) Date of Patent: Nov. 3, 2026

(54) VIRULENCE FACTOR FsPL GENE FROM SUGARCANE POKKAH BOENG DISEASE AND USE THEREOF

(71) Applicant: GUANGXI UNIVERSITY, Nanning (CN)

(72) Inventors: Wei Yao, Nanning (CN); Zhen Huang, Nanning (CN); Zhenzhen Duan, Nanning (CN); Muqing Zhang, Nanning (CN); Caixia Wang, Nanning (CN); Yixue Bao, Nanning (CN); Huixue Li, Nanning (CN)

(73) Assignee: GUANGXI UNIVERSITY, Nanning (CN)

( * ) Notice: Subject to any disclaimer, the term of this patent is extended or adjusted under 35 U.S.C. 154(b) by 680 days.

(21) Appl. No.: 18/184,721

(22) Filed: Mar. 16, 2023

(65) Prior Publication Data

US 2024/0099311 A1 Mar. 28, 2024

(30) Foreign Application Priority Data

Sep. 16, 2022 (CN) ......................... 202211125577.6

(51) Int. Cl.

| | |
|---|---|
| ***C07K 14/37*** | (2006.01) |
| ***A01N 63/50*** | (2020.01) |
| ***A01P 3/00*** | (2006.01) |
| ***C12N 1/20*** | (2026.01) |
| ***C12N 15/74*** | (2006.01) |

(52) U.S. Cl.

CPC ................ *A01N 63/50* (2020.01); *A01P 3/00* (2021.08); *C07K 14/37* (2013.01); *C12N 1/20* (2013.01); *C12N 15/74* (2013.01); *C12N 2800/101* (2013.01)

(58) Field of Classification Search

CPC ........... A01N 63/50; A01P 3/00; C07K 14/37; C12N 15/74; C12N 1/20; C12N 2800/101

See application file for complete search history.

(56) References Cited

U.S. PATENT DOCUMENTS 6,864,404 B1 * 3/2005 Vogel ................. C12N 15/8282 536/23.6
10,676,751 B2 * 6/2020 Daniell .......... C12Y 302/01021

OTHER PUBLICATIONS

NPL_Wang_2023_pectate-lyase-contributes-to-virulence.pdf (Year: 2023).*
NPL_Huang_2022_Predication_of_the_Effector_Proteins_Secreted_by_Fusarium_sacchari.pdf (Year: 2022).*
Wegener_1996_Pectate_lyase_in_transgenic_potatoes. (Year: 1996).*
Yang_2018_A_Verticillium_dahliae_Pectate_Lyase_Induces_Plant_Immune_Responses (Year: 2018).*
Title of the Item: Northwest A&F University Publication Date: May 2013 Name of the Author: Chunlei Tang Article Title: Identification and Functional Analysis of Effector Proteins and Genes Inducing Host Cell Necrosis in Interactions of Puccinia striiformis with Wheat.
Title of the Item: Acta Phytopathologica Sinica Publication Date: Jul. 12, 2019 Name of the Author: Likun Wang, Xin Fan, Chunlei Tang, Zhensheng Kang, Xiaojie Wang Article Title: Inhibition of Accumulation of Callose and Reactive Oxygen Species in Plants by Puccinia striiformis Effector Pst30.

* cited by examiner

*Primary Examiner* — Neil P Hammell
*Assistant Examiner* — Delphinus Dou Yi Yu
(74) *Attorney, Agent, or Firm* — Nitin Kaushik

(57) ABSTRACT

A virulence factor FsPL gene from the sugarcane pokkah boeng disease and use thereof are provided. The virulence factor FsPL gene from the sugarcane pokkah boeng disease has a sequence set forth in SEQ ID NO: 1. The present invention reveals a gene FsPL that is related to the pathogenicity of *F. sacchari*. Preliminary analysis shows that the deletion of the gene affects the ability of hyphae to penetrate and further affects the pathogenicity of pathogens. This provides a basis for the molecular mechanism of the pathogen infection and pathogenic process.

1 Claim, 7 Drawing Sheets

Specification includes a Sequence Listing.

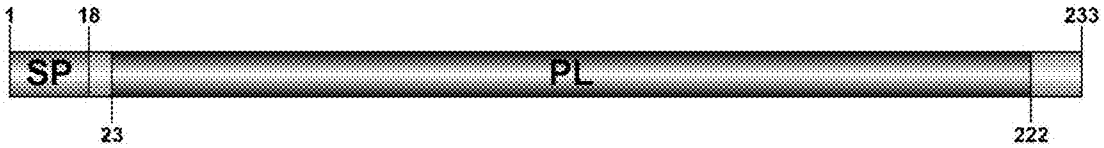
FIG. 1
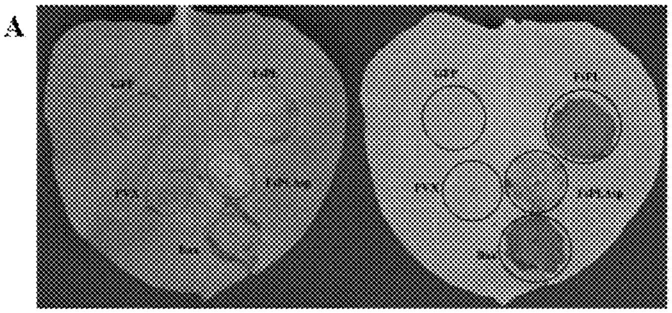
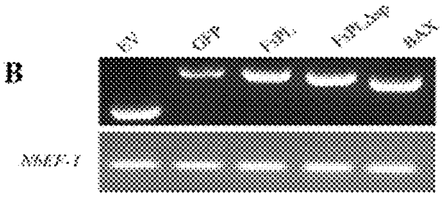
FIG. 2A
FIG. 2B
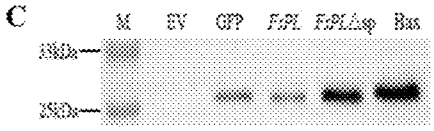
FIG. 2C

| Barrel 1 [a] | Barrel 2 [a] | Direct ratio [b] | P value [c] |
|---|---|---|---|
| GUS+Bax | GUS+EV | 0.11 ± 0.02 | P<0.01 |
| GUS+FsPL | GUS+EV | 0.24 ± 0.04 | P<0.01 |
| GUS+FsPLΔsp | GUS+EV | 0.48 ± 0.04 | P<0.05 |

SEQUENCE LISTING

```
Sequence total quantity: 29
SEQ ID NO: 1            moltype = DNA  length = 702
FEATURE                 Location/Qualifiers
source                  1..702
                        mol_type = other DNA
                        organism = synthetic construct
SEQUENCE: 1
atgcacgcct ccagccttct caccctcctc accaccctcc ccgccgcaat ggcctgtctc  60
ggctacaccg gcggcgtccc caaagctaca ggcaccaagt ccctcagcgc cccccaatac  120
ctcaagaagg gccaagtctt cgacgcaaag tgggttcgct acgaccgcgg cgtcaagtgc  180
tctggccaga gcgaaggcgg cgagaaggac gctgtgttcg ttctcgagga cggcgctact  240
cttcgcaatg ttgtcatcgg tgcgaaccag aaggagggcg tgcactgtct tggtgcttgt  300
aaccttgagt ttgtctggtt tgaggatgtt tgtgaggatg ctatctctat caagggtagt  360
ggaactgcca acattattgg tggcggtgcg tacaaggctg ccgataaggt tattcagcac  420
aatggatgcg gccacgtcaa cattgtcaac ttctatgcca acgactatgg caaggtctac  480
cgctcctgcg gtaactgcaa gggtaactcc aactgcaagc gatcagtcca catggagggc  540
gtcactgctg tcaacggcgg tgagctcatg ggcatcaaca ccaacctcgg tgacaaggct  600
acttactcca acaactgcta ccccaagact cagtgccagg gctacaacgg ctgcgacaag  660
tccaacggcg agtgtgagcc taccaaggct ggcaagtgct ag                    702

SEQ ID NO: 2            moltype = AA  length = 233
FEATURE                 Location/Qualifiers
source                  1..233
                        mol_type = protein
                        organism = synthetic construct
SEQUENCE: 2
MHASSLLTLL TTLPAAMACL GYTGGVPKAT GTKSLSAPQY LKKGQVFDAK WVRYDRGVKC  60
SGQSEGGEKD AVFVLEDGAT LRNVVIGANQ KEGVHCLGAC NLEFVWFEDV CEDAISIKGS  120
GTANIIGGGA YKAADKVIQH NGCGHVNIVN FYANDYGKVY RSCGNCKGNS NCKRSVHMEG  180
VTAVNGGELM GINTNLGDKA TYSNNCYPKT QCQGYNGCDK SNGECEPTKA GKC         233

SEQ ID NO: 3            moltype = DNA  length = 48
FEATURE                 Location/Qualifiers
source                  1..48
                        mol_type = other DNA
                        organism = synthetic construct
SEQUENCE: 3
agcaccagct agcatcgata tgagtaaagg agaagaactt ttcactgg              48

SEQ ID NO: 4            moltype = DNA  length = 52
FEATURE                 Location/Qualifiers
source                  1..52
                        mol_type = other DNA
                        organism = synthetic construct
SEQUENCE: 4
atcgtatggg tacgcggccg ctttgtatag ttcatccatg ccatgtgtaa tc          52
```

```
SEQ ID NO: 5            moltype = DNA  length = 36
FEATURE                 Location/Qualifiers
source                  1..36
                        mol_type = other DNA
                        organism = synthetic construct
SEQUENCE: 5
agcaccagct agcatcgata tggacgggtc cgggga                      36

SEQ ID NO: 6            moltype = DNA  length = 43
FEATURE                 Location/Qualifiers
source                  1..43
                        mol_type = other DNA
                        organism = synthetic construct
SEQUENCE: 6
atcgtatggg tacgcggccg cgcccatctt cttccagatg gtg              43

SEQ ID NO: 7            moltype = DNA  length = 36
FEATURE                 Location/Qualifiers
source                  1..36
                        mol_type = other DNA
                        organism = synthetic construct
SEQUENCE: 7
agcaccagct agcatcgata tgcacgcctc cagcct                      36

SEQ ID NO: 8            moltype = DNA  length = 41
FEATURE                 Location/Qualifiers
source                  1..41
                        mol_type = other DNA
                        organism = synthetic construct
SEQUENCE: 8
atcgtatggg tacgcggccg cctagcactt gccagccttg g                41

SEQ ID NO: 9            moltype = DNA  length = 40
FEATURE                 Location/Qualifiers
source                  1..40
                        mol_type = other DNA
                        organism = synthetic construct
SEQUENCE: 9
agcaccagct agcatcgata tgtgtctcgg ctacaccggc                  40

SEQ ID NO: 10           moltype = DNA  length = 21
FEATURE                 Location/Qualifiers
source                  1..21
                        mol_type = other DNA
                        organism = synthetic construct
SEQUENCE: 10
tggtgtcctc aagcctggta t                                      21

SEQ ID NO: 11           moltype = DNA  length = 21
FEATURE                 Location/Qualifiers
source                  1..21
                        mol_type = other DNA
                        organism = synthetic construct
SEQUENCE: 11
acgcttgaga tccttaaccg c                                      21

SEQ ID NO: 12           moltype = DNA  length = 37
FEATURE                 Location/Qualifiers
source                  1..37
                        mol_type = other DNA
                        organism = synthetic construct
SEQUENCE: 12
aggtcgactc tagaggatcc atggacgggt ccgggga                     37

SEQ ID NO: 13           moltype = DNA  length = 38
FEATURE                 Location/Qualifiers
source                  1..38
                        mol_type = other DNA
                        organism = synthetic construct
SEQUENCE: 13
acatacgcgt ggtaccgccc atcttcttcc agatggtg                    38

SEQ ID NO: 14           moltype = DNA  length = 37
FEATURE                 Location/Qualifiers
source                  1..37
                        mol_type = other DNA
                        organism = synthetic construct
SEQUENCE: 14
```

```
aggtcgactc tagaggatcc atgcacgcct ccagcct                          37

SEQ ID NO: 15          moltype = DNA  length = 36
FEATURE                Location/Qualifiers
source                 1..36
                       mol_type = other DNA
                       organism = synthetic construct
SEQUENCE: 15
acatacgcgt ggtaccctag cacttgccag ccttgg                           36

SEQ ID NO: 16          moltype = DNA  length = 41
FEATURE                Location/Qualifiers
source                 1..41
                       mol_type = other DNA
                       organism = synthetic construct
SEQUENCE: 16
aggtcgactc tagaggatcc atgtgtctcg gctacaccgg c                     41

SEQ ID NO: 17          moltype = DNA  length = 23
FEATURE                Location/Qualifiers
source                 1..23
                       mol_type = other DNA
                       organism = synthetic construct
SEQUENCE: 17
gactggcgaa ataaccagat cga                                         23

SEQ ID NO: 18          moltype = DNA  length = 26
FEATURE                Location/Qualifiers
source                 1..26
                       mol_type = other DNA
                       organism = synthetic construct
SEQUENCE: 18
atgtttgtat cggcttgata ttgctc                                      26

SEQ ID NO: 19          moltype = DNA  length = 18
FEATURE                Location/Qualifiers
source                 1..18
                       mol_type = other DNA
                       organism = synthetic construct
SEQUENCE: 19
tctggcggtt gggagagt                                               18

SEQ ID NO: 20          moltype = DNA  length = 24
FEATURE                Location/Qualifiers
source                 1..24
                       mol_type = other DNA
                       organism = synthetic construct
SEQUENCE: 20
cgaggcattc ttgggtcatt ttag                                        24

SEQ ID NO: 21          moltype = DNA  length = 21
FEATURE                Location/Qualifiers
source                 1..21
                       mol_type = other DNA
                       organism = synthetic construct
SEQUENCE: 21
cggtacccgg ggatcctcta g                                           21

SEQ ID NO: 22          moltype = DNA  length = 22
FEATURE                Location/Qualifiers
source                 1..22
                       mol_type = other DNA
                       organism = synthetic construct
SEQUENCE: 22
gcctgcaggt cgacagaaga tg                                          22

SEQ ID NO: 23          moltype = DNA  length = 20
FEATURE                Location/Qualifiers
source                 1..20
                       mol_type = other DNA
                       organism = synthetic construct
SEQUENCE: 23
ggagcttggc gttacctgtc                                             20

SEQ ID NO: 24          moltype = DNA  length = 21
FEATURE                Location/Qualifiers
source                 1..21
                       mol_type = other DNA
                       organism = synthetic construct
```

```
SEQUENCE: 24
gggagacgag atcaagcaga t                                            21

SEQ ID NO: 25          moltype = DNA  length = 20
FEATURE                Location/Qualifiers
source                 1..20
                       mol_type = other DNA
                       organism = synthetic construct
SEQUENCE: 25
tcgcgcatat gaaatcacgc                                              20

SEQ ID NO: 26          moltype = DNA  length = 20
FEATURE                Location/Qualifiers
source                 1..20
                       mol_type = other DNA
                       organism = synthetic construct
SEQUENCE: 26
cctcccgctc caataagcat                                              20

SEQ ID NO: 27          moltype = DNA  length = 1105
FEATURE                Location/Qualifiers
source                 1..1105
                       mol_type = other DNA
                       organism = synthetic construct
SEQUENCE: 27
gactggcgaa ataaccagat cgagctcacc aaggctatcg ttgacgaggg ttgggctact  60
cttgctgatg tcttcaaggt tgaggactgt gctggcaagg agcctacctt caacggcaag  120
gagcttggcg ttacctgtct cgtaagtcaa cctggactgc ctaatggatt aaaaacgcta  180
atgatctggt taggctaccc acaactggtg cgagtggaac taccaggact ctcctgggct  240
gtctcgtgag gagcctcagt ggaagaactg cgacaacgac gacaagtggg gaactctctg  300
cggaagcttc cagagcggac tcgagagtaa gtctttctta tgccgcatca tctgcacaaa  360
ttcgagacta atggatctga aacagttccc gaatcttacc ttggtcctct cctcaacagc  420
gaccaaacct ggtgcaagcg atagatttcg aacaccaaga cttgacattg tggtcaagta  480
gcagtattgc agttgcccag agttcacttg gatcacccctt tgaagttctg tttatagcta  540
gggtcgcggg ttcagtagcg ttcactggaa agctttgtac tataacttgg aagccgactg  600
gatggagatg gagttgaggt agagttggta gttggatatt tcgcaatgca atttggtcaa  660
ccacgttcct gaagctcaat tacaacggtc gctcgatatc atgacatatc taaacccatc  720
ataggtttgc aaggaagcca agcccacttt gatctcgggc tactgatggg tgtttggaga  780
gtgctatcat gagttaagaa gcctaagcgt gacagttggc gctggaatcg aaattatttt  840
acctcaggct ccacaaggct cttgtaggtt gatgaggaat actcaagtgt agtcctgaga  900
gccgcatata tcggcatatt tgcaagtcct gaaagttagg gataagaagg aacgtagtag  960
aagtgacata gatgtgcagt tatctaaagt cataatatac acagcaggca agaggcgact  1020
tagtaccagt tctaggctcc aaccagccaa ttaaagaagg tgatacacac ttgctaccag  1080
agcaatatca agccgataca aacat                                        1105

SEQ ID NO: 28          moltype = DNA  length = 1015
FEATURE                Location/Qualifiers
source                 1..1015
                       mol_type = other DNA
                       organism = synthetic construct
SEQUENCE: 28
tctggcggtt gggagagtgg tgagtggtag gttgaagaga agccggtcaa cggttgatga  60
gtcgtgaaga tagaagcgaa tgtcaatgca gagagatgaa ggtgagctgg tggggactga  120
gtaactagag aggaactagc tatccttctt atacaagctg tctcttctgc ttcgcgatca  180
atccgagcga gtacgatcca tccatgttat cccaacacca tggttctcag caagtcaccc  240
actaattcta attcgcctac cctcctcccc cccatctcca tcaatcagaa caaacagcat  300
catccgcttt acgaaaataa aataaggtgt ccagctcctc gtttcaggac gatccatttc  360
ctccacttag gtgacggaca gtccagcgct gataggctag tcagagctga catcccagtc  420
gaatgtttgg ggatgcgcgt atttgactta agcttatttc gggttcggat gactgaaccg  480
ctttcagaca cgatgaccgg atatggaggc tgtgctggtg agatgatcgt taaaatccga  540
gattttgtgg agtgcaggca ttgagttgtt tcgaatcatc cgatatgctt attggagcgg  600
gaggtcctcg cagagatgac tgcggatatg attggtggtg aaatttgttg gtcttttggc  660
accgatagtg cgacttccga tacggagcgg aatactgact ccggtgatgt ttgggagagc  720
tcaaggcaaa tcatgctcgg tgagctcttc gccgaatgat gaacacgaga tgaaagtacg  780
gatacgtagc catgggagat attatccgat tcagagagta ccgcccaagt cccagaccta  840
gccaaggtaa agcagcctat ggattccgtg ttcgcgactc tcgataaatt gggacagttt  900
ttgatcaagg agccggactc aaaaacggac cgtaccgaag aatgtactca aaaatgtcat  960
cgcttcgtgt tgaatcgggg aataactcac actaaaatga cccaagaatg cctcg       1015

SEQ ID NO: 29          moltype = DNA  length = 2145
FEATURE                Location/Qualifiers
source                 1..2145
                       mol_type = other DNA
                       organism = synthetic construct
SEQUENCE: 29
cggtacccgg ggatcctcta gaaagaagga ttacctctaa acaagtgtac ctgtgcattc  60
tgggtaaacg actcatagga gagttgtaaa aaagtttcgg ccggcgtatt gggtgttacg  120
gagcattcac taggcaacca tggttactat tgtataccat cttagtagga atgatttcga  180
ggtttatacc tacgatgaat gtgtgtcctg taggcttgag agttcaagga agaaacatgc  240
```

-continued

```
aattatcttt gcgaacccag ggctggtgac ggaattttca tagtcaagct atcagagtaa  300
agaagaggag catgtcaaag tacaattaga gacaaatata tagtcgcgtg gagccaagag  360
cggattcctc agtctcgtag gtctcttgac gaccgttgat ctgcttgatc tcgtctcccg  420
aaaatgaaaa tagctctgct aagctattct tctcttcgcc ggagcctgaa ggcgttacta  480
ggttgcagtc aatgcattaa tgcattgcag atgagctgta tctggaagag gtaaacccga  540
aaacgcgttt tattcttgtt gacatggagc tattaaatca ctagaaggca ctctttgctg  600
cttggacaaa tgaacgtatc ttatcgagat cctgaacacc atttgtctca actccggagc  660
tgacatcgac accaacgatc ttatatccag attcgtcaag ctgtttgatg atttcagtaa  720
cgttaagtgg atggatccat ctactctatt cctttgccct cggacgagtg ctggggcgtc  780
ggtttccact atcggcgagt acttctacac agccatcggt ccagacggcc gcgcttctgc  840
gggcgatttg tgtacgcccg acagtcccgg ctccggatcg gacgattgcg tcgcatcgac  900
cctgcgccca agctgcatca tcgaaattgc cgtcaaccaa gctctgatag agttggtcaa  960
gaccaatgcg gagcatatac gcccggagcc gcggcgatcc tgcaagctcc ggatgcctcc  1020
gctcgaagta gcgcgtctgc tgctccatac aagccaacca cggcctccag aagaagatgt  1080
tggcgacctc gtattgggaa tccccgaaca tcgcctcgct ccagtcaatg accgctgtta  1140
tgcggccatt gtccgtcagg acattgttgg agccgaaatc cgcgtgcacg aggtgccgga  1200
cttcggggca gtcctcggcc caaagcatca gctcatcgag agcctgcgcg acggacgcac  1260
tgacggtgtc gtccatcaca gtttgccagt gatacacatg gggatcagca atcgcgcata  1320
tgaaatcacg ccatgtagtg tattgaccga ttccttgcgg tccgaatggg ccgaacccgc  1380
tcgtctggct aagatcggcc gcagcgatcg catccatggc ctccgcgacc ggctgcagaa  1440
cagcgggcag ttcggtttca ggcaggtctt gcaacgtgac accctgtgca cggcgggaga  1500
tgcaataggt caggctctcg ctgaattccc caatgtcaag cacttccgga atcgggagcg  1560
cggccgatgc aaagtgccga taaacataac gatctttgta gaaaccatcg gcgcagctat  1620
ttacccgcag gacatatcca cgccctccta catcgaagct gaaagcacga gattcttcgc  1680
cctccgagag ctgcatcagg tcggagacgc tgtcgaactt ttcgatcaga aacttctcga  1740
cagacgtcgc ggtgagttca ggctttttca tatcgatgct tcggtagaat aggtaagtca  1800
gattgaatct gaaataaagg gaggaagggc gaacttaaga aggtatgacc gggtcgttca  1860
cttaccttgc ttgacaaacg cacaagttat cgtgcaccaa gcagcagatg ataataatgt  1920
cctcgttcct gtctgctaat aagagtcaca cttcgagcgc cgccgctact gcttacaagt  1980
gggctgatct gaccagttgc ctaaatgaac catcttgtca aacgacacaa attttgtgat  2040
ccgcctggac gactaaacca aaatagcatt gatgtgttga cctccactag ctccagccaa  2100
gcccaaaaat gctccttcaa tatcatcttc tgtcgacctg caggc                  2145
```

VIRULENCE FACTOR FsPL GENE FROM SUGARCANE POKKAH BOENG DISEASE AND USE THEREOF

CROSS REFERENCE TO THE RELATED APPLICATIONS

This application is based upon and claims priority to Chinese Patent Application No. 202211125577.6, filed on Sep. 16, 2022, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBRZBC079_Sequence_Listing.xml, created on Mar. 13, 2023, and is 31,814 bytes in size.

TECHNICAL FIELD

The present invention relates to the technical field of genetic engineering and in particular, to a virulence factor FsPL gene from the sugarcane pokkah boeng disease and use thereof.

BACKGROUND

Pokkah boeng disease (PBD), a widespread fungal disease of sugarcane caused by *Fusarium sacchari* and other *Fusarium* species with a relatively high incidence, mainly attacks the young leaves at the top of sugarcane. It causes, in a mild case, chlorosis and distortion of the leaves at the top of sugarcane and, in a severe case, a deformity of and necrosis in the whole top part, which lead to top rot and even the death of the whole sugarcane plant. In recent years, as large areas of sugarcane cultivars susceptible to the pokkah boeng disease have been planted, the incidence of the pokkah boeng disease in sugarcane areas has been increasing and trending upward, causing heavy yield losses (about 10-40%) in sugarcane production.

The plant cell wall is the initial physical and defensive barrier against a variety of biological stresses. As an important site where a host interacts with pathogens, the plant cell wall is often dynamically remodeled to produce immune responses, preventing pathogen infection. It also participates in sensing external stressors and transmits corresponding signals to stimulate defense responses. The plant cell wall is a complex network of polysaccharides such as cellulose, hemicellulose and pectin. To successfully infect a host, plant pathogens produce a series of cell-wall degrading enzymes (CWDEs), including cellulases, pectinases, xylanases, xyloglucanases, and the like, which physically disintegrate the plant cell wall, helping themselves penetrate host cells and spread throughout the plant's tissues. The oligosaccharides such as cellodextrins, oligogalacturonic acids (OGAs) and xyloglucan oligosaccharides produced from the action of CWDs on the cell walls of the plant can serve as elicitors to trigger the plant's defense responses against the infection with pathogens. Plant's defense responses include PTI and ETI. The immune response triggered on the recognition of PAMPs or DAMPs by the pattern recognition receptors (PRRs) on plant cell surfaces is a basic defense response in a plant termed PTI. Typical PTI includes bursts of reactive oxygen species, callose accumulation, electrolyte leakage, etc., by which microorganisms are typically confined to the site of infection. As typical DAMPs, the oligogalacturonic acids (OGAs) produced by the pectate lyase cleavage of polygalacturonic acids via a β-elimination reaction can be recognized by WAK1, a plasma membrane-associated protein on the plant-cell surface, activating the MAPK cascade; the MAPK cascade increases free cytosolic calcium levels and promotes ROS generation, triggering PTI responses. However, pathogens can interfere with or disrupt PTI by secreting effector proteins that enhance pathogen virulence. In the process of evolution, plants utilize R protein to directly or indirectly recognize these effectors, thereby triggering the second-line defense response—ETI (effector-triggered immunity) response. One of the most notable features of ETI is to trigger the hypersensitive response (HR) in plants—that is, producing defense proteins that induce rapid programmed cell death at the site of pathogen attack to limit pathogen transmission. This division between PAMPs and effectors, or between PTI and ETI, is, however, blurred and has been challenged recently.

Pectate lyase is an important enzyme secreted by plant pathogens and has been reported in a variety of microorganisms. Pectate lyase was found earlier in a variety of bacteria such as *Erwinia carotovora, Enwinia chrysanthemi, Erwinia chrysanthemi* and *Pseudomonas solanacearum*. The pectate lyase genes have also been studied in fungi. BcSpl1 contributes to the virulence of *Botrytis cinerea* and elicits hypersensitive responses in the host. VdPL1-4 is an important virulence factor for *Verticillium dahliae*; it plays an important role in the pathogenic process of the pathogenic bacterium. Vmpl4 is involved in the pathogenic process of *Valsa mali*. The deletion of the CcpelA gene affects the infectivity of *Colletotrichum coccodes*.

Therefore, the research on the role the pectate lyase gene FsPL plays in the pathogenic process of *Fusarium sacchari* is of great significance for the further understanding of the pathogenic mechanism of the bacterium and provides a theoretical basis for the prevention and treatment of PBD.

SUMMARY

The present invention aims to provide a virulence factor FsPL gene from the sugarcane pokkah boeng disease and use thereof. The present invention reveals a gene FsPL that is related to the pathogenicity of *F. sacchari*. Preliminary analysis shows that the deletion of the gene affects the ability of hyphae to penetrate and further affects the pathogenicity of pathogens. This provides a basis for the molecular mechanism of the pathogen infection and pathogenic process.

To achieve the aim described above, the present invention provides the following technical solutions.

The present invention provides a virulence factor FsPL gene from the sugarcane pokkah boeng disease, which is from the common pathogens of pokkah boeng disease, and the virulence factor FsPL gene from the sugarcane pokkah boeng disease has a sequence set forth in SEQ ID NO: 1.

The present invention also provides a protein encoded by a virulence factor FsPL gene from the sugarcane pokkah boeng disease, and the protein has an amino acid sequence set forth in SEQ ID NO: 2.

The present invention also provides a silencing vector, which comprises an original vector and the FsPL gene.

The present invention also provides a silent recombinant bacterium, which is transformed or transfected with the silencing vector.

The present invention also provides a primer pair for cloning the sequence of the virulence factor FsPL gene from the sugarcane pokkah boeng disease, and the primer pair is one of a PVX-FsPL primer pair, a PVX-FsPLΔSP primer pair, a pCAMBIA2300-FsPL primer pair, and a pCAMBIA2300-FsPLΔSP primer pair;

a forward primer of PVX-FsPL has a nucleotide sequence set forth in SEQ ID NO: 7;

a reverse primer of PVX-FsPL has a nucleotide sequence set forth in SEQ ID NO: 8;

a forward primer of PVX-FsPLΔSP has a nucleotide sequence set forth in SEQ ID NO: 9;

a reverse primer of PVX-FsPLΔSP has a nucleotide sequence set forth in SEQ ID NO: 8;

a forward primer of pCAMBIA2300-FsPL has a nucleotide sequence set forth in SEQ ID NO: 14;

a reverse primer of pCAMBIA2300-FsPL has a nucleotide sequence set forth in SEQ ID NO: 15;

a forward primer of pCAMBIA2300-FsPLΔSP has a nucleotide sequence set forth in SEQ ID NO: 16;

a reverse primer of pCAMBIA2300-FsPLΔSP has a nucleotide sequence set forth in SEQ ID NO: 15.

The present invention further provides use of the FsPL gene, the protein, the silencing vector and the silent recombinant bacterium in manufacturing a peptide medicament against sugarcane pokkah boeng fungi.

Compared to the prior art, the present invention has the following advantages:

(1) The present invention starts with the genome of the pathogenic bacterium and provides an FsPL gene comprising a pectate lyase domain through analysis. Preliminary verification reveals that the gene can elicit PCD response in *Nicotiana benthamiana* and maize and can elicit PTI response in *Nicotiana benthamiana*. This indicates that the protein may be an elicitor capable of inducing immunity in plants, providing a reference for environmentally friendly control in sugarcane.

(2) The present invention reveals a gene FsPL that is related to the pathogenicity of *F. sacchari*. Preliminary analysis shows that the deletion of the gene affects the ability of hyphae to penetrate and further affects the pathogenicity of pathogens. This provides a basis for the molecular mechanism of the pathogen infection and pathogenic process.

BRIEF DESCRIPTION OF THE DRAWINGS

In order to more clearly illustrate the technical solutions in the examples of the present invention or in the prior art, the drawings required to be used in the description of the examples or the prior art are briefly introduced below. It is obvious that the drawings in the description below are merely examples of the present invention, and those of ordinary skilled in the art can obtain other drawings according to the drawings provided without creative efforts.

FIG. 1: a graph showing the structure of the gene comprising a pectate lyase PL domain of the present invention;

graphing and analysis of the structure of the gene are performed using software IBS 1.0, and the positions of the signal peptide region and the domain are indicated.

FIGS. 2A-2C: a graph showing the *Agrobacterium*-mediated transient expression in tobacco leaves according to the present invention;

*Agrobacterium* carrying a recombinant vector is allowed to permeate into tobacco leaves by injection, and the sites of injection are marked; after 7 d, the symptoms are observed and photographed (photographic records are made before and after decoloring) (in FIG. 2A), during which attention is paid to symptom changes; a sample is collected from each of the sites 48 h after infection, RNA is extracted and then reverse-transcribed, and the gene transcription is monitored by RT-PCR (in FIG. 2B); total protein is extracted and then tested by Western blot to examine how is the protein translation (in FIG. 2C).

Figure 3A:
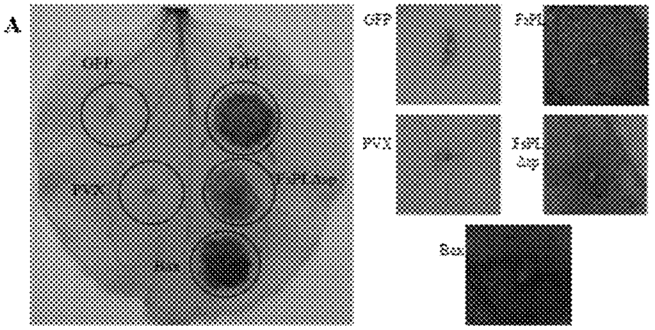
Figure 3B:
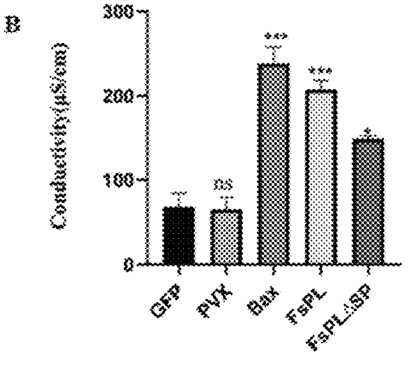

FIGS. 3A-3B: a graph showing PTI response elicited by the FsPL of the present invention in tobacco leaves;

reactive oxygen species staining is performed using DAB (in FIG. 3A), electrolyte leakage is measured on a conductivity meter (in FIG. 3B), and callose staining is performed using aniline blue (in FIG. 3C); it is found that FsPL can induce typical PTI response in *Nicotiana benthamiana* leaves.

Figure 4:
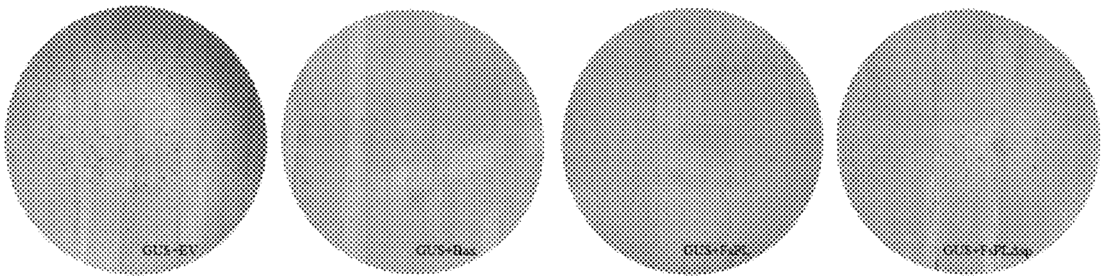

FIG. 4: a graph showing the gene gun-mediated transient expression in maize leaves according to the present invention;

the GUS gene is mixed with the gene to be verified, and the mixed genes are co-transformed into maize leaves by gene gun bombardment; after 2 d, GUS staining is performed, pictures are taken, and the blue spots are counted; it is found that the FsPL gene can elicit PCD response in maize leaves.

Figure 5:
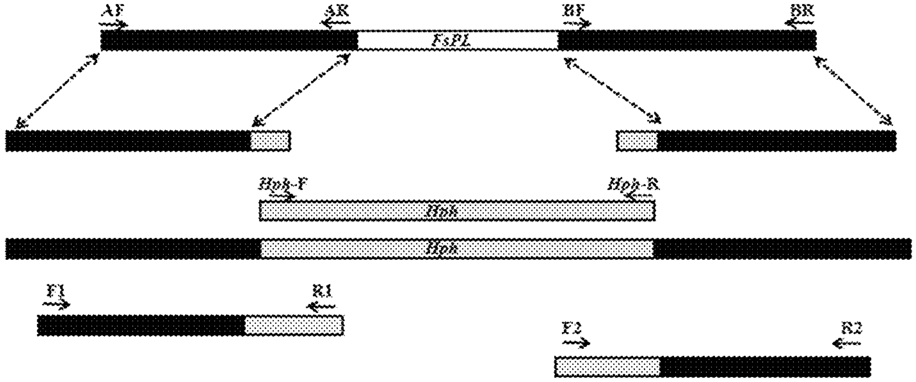

FIG. 5: a graph showing a gene knockout strategy and the relative position of each primer.

Figure 6:
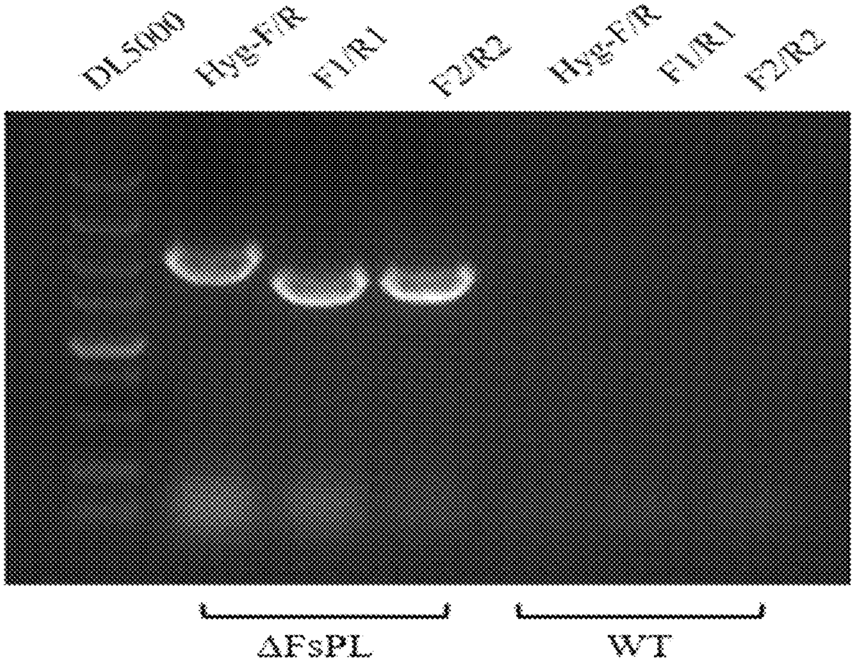

FIG. 6: a graph showing the detection of positive transformants by three pairs of primers (Hph-F/R, FsPL-F1+Hph-R1, Hph-F2+FsPL-R2).

Figure 7:
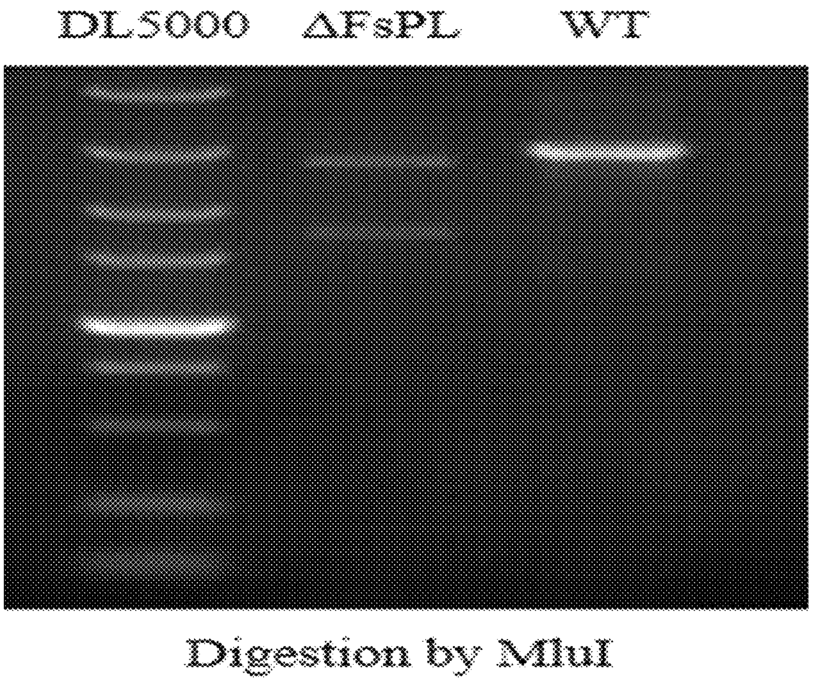

FIG. 7: a graph showing MluI digestion verification of different test groups.

Figure 8:
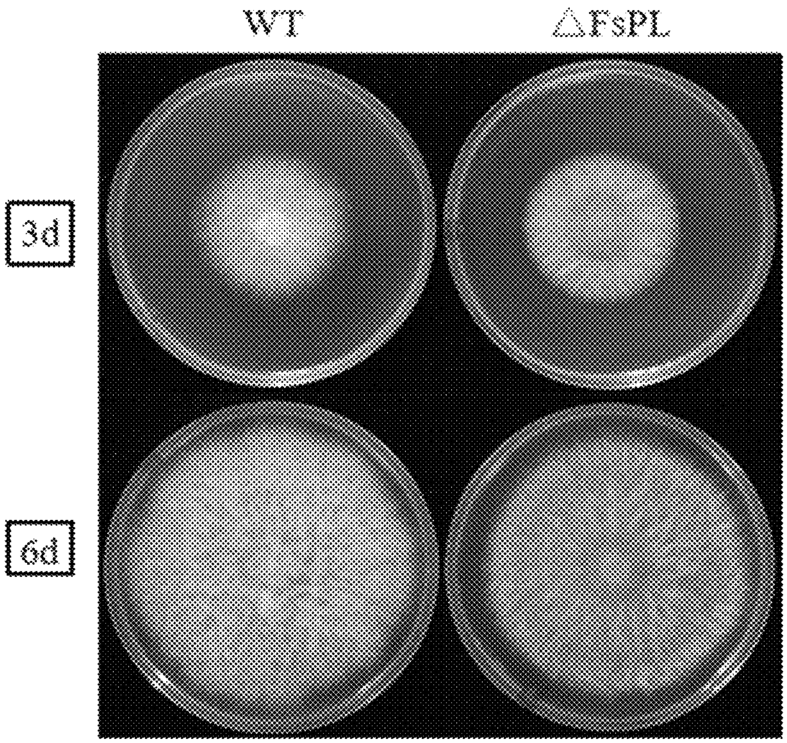

FIG. 8: a graph for the phenotype observation of the wild type and mutant in PDA media; the mutant strain ΔFsPL is obtained based on homologous recombination and protoplast transformation.

Figure 9:
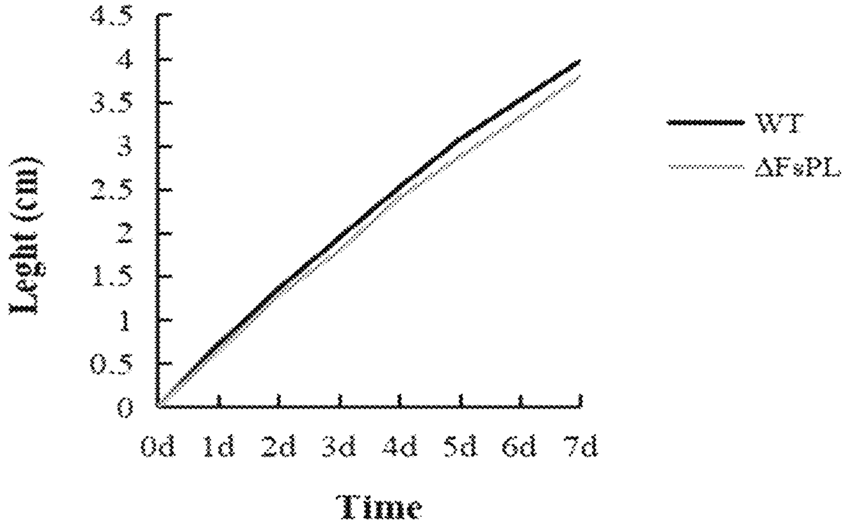

FIG. 9: a graph showing the rate of growth of hyphae of different test groups.

Figure 10:
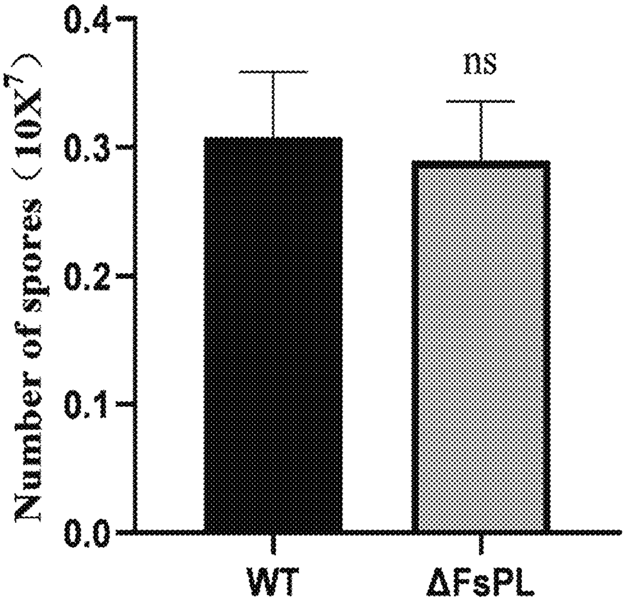

FIG. 10: a graph showing the number of conidia of the mutant and wild type counted using a hemocytometer; the conidia of the bacteria are cultured in CMC media.

Figure 11:
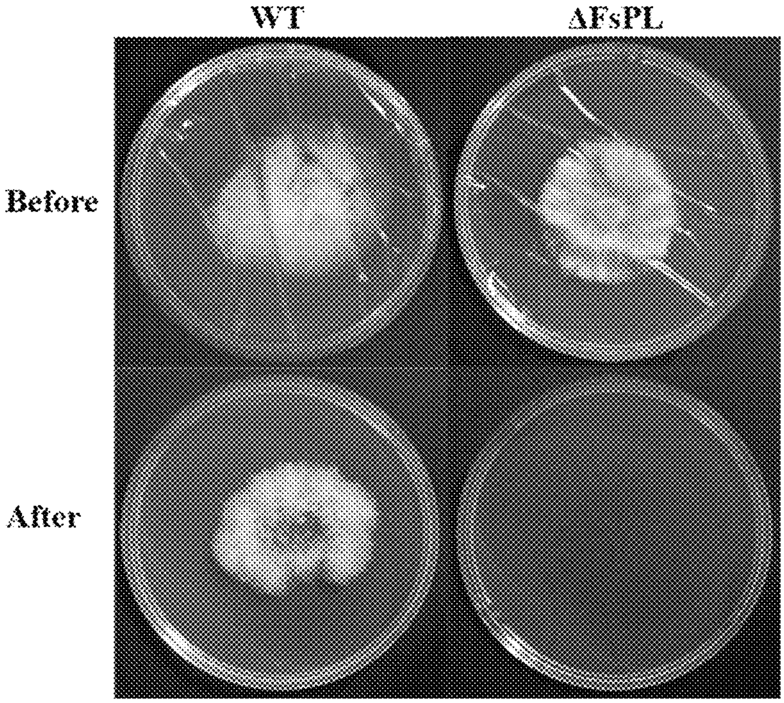

FIG. 11: a graph showing cellophane penetration experiments of different test groups.

Figure 12:
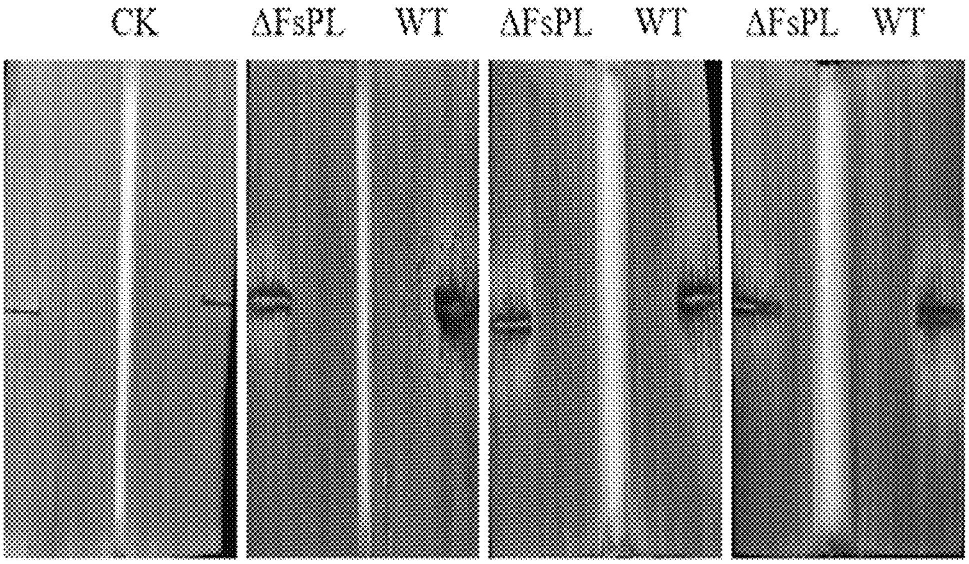

FIG. 12: a graph showing in-vitro inoculation pathogenicity analysis of different test groups.

Figure 13:
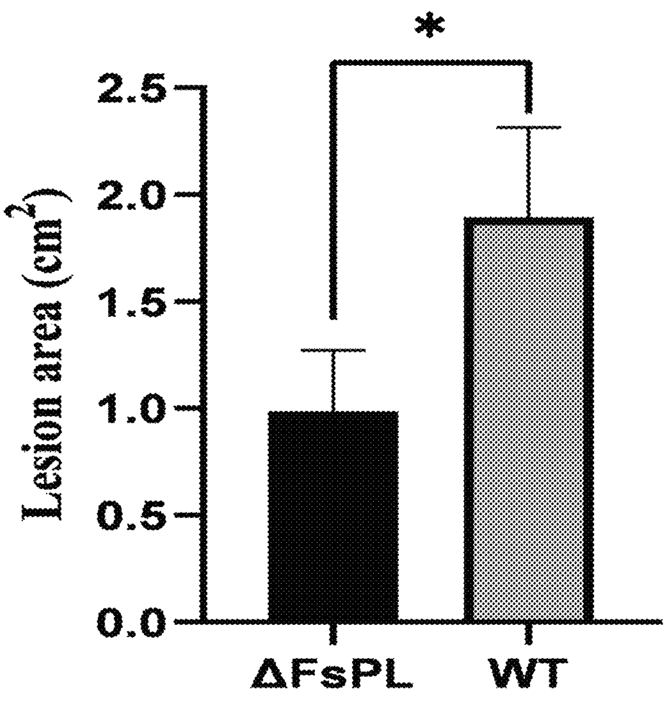

FIG. 13: a statistical graph of necrosis area on sugarcane leaves of different test groups.

Figure 14A:
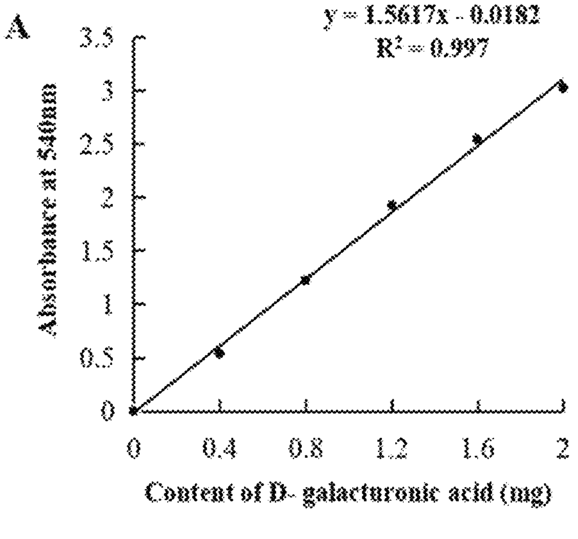
Figure 14B:
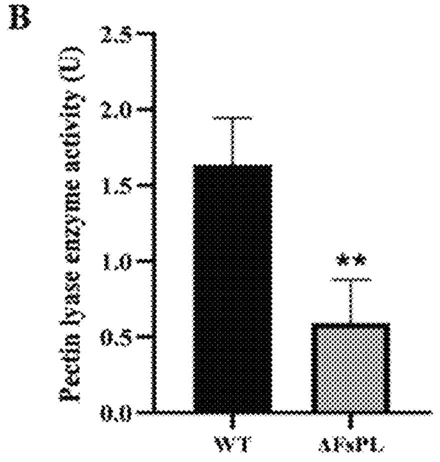

FIGS. 14A-14B: an assay for the activity of pectate lyase; a D-galacturonic acid standard curve (in FIG. 14A); an assay for the extracellular pectate lyase activity of the mutant and wide type, where  indicates a very significant difference ($P<0.01$) (in FIG. 14**B).

DETAILED DESCRIPTION OF THE EMBODIMENTS

The present invention provides a virulence factor FsPL gene from the sugarcane pokkah boeng disease, which is from the common pathogens of pokkah boeng disease, and the virulence factor FsPL gene from the sugarcane pokkah boeng disease has a sequence set forth in SEQ ID NO: 1.

The present invention also provides a protein encoded by a virulence factor FsPL gene from the sugarcane pokkah boeng disease, and the protein has an amino acid sequence set forth in SEQ ID NO: 2.

The present invention also provides an upstream nucleotide sequence and a downstream nucleotide sequence of FsPL as set forth in SEQ ID NO: 27 and SEQ ID NO: 28.

The present invention also provides an Hph sequence as set forth in SEQ ID NO: 29.

The present invention also provides a silencing vector, which comprises an original vector and the FsPL gene.

The present invention also provides a silent recombinant bacterium, which is transformed or transfected with the silencing vector.

The present invention also provides a primer pair for cloning the sequence of the virulence factor FsPL gene from the sugarcane pokkah boeng disease, and the primer pair is one of a PVX-FsPL primer pair, a PVX-FsPLΔSP primer pair, a pCAMBIA2300-FsPL primer pair, and a pCAMBIA2300-FsPLΔSP primer pair;

a forward primer of PVX-FsPL has a nucleotide sequence set forth in SEQ ID NO: 7;

a reverse primer of PVX-FsPL has a nucleotide sequence set forth in SEQ ID NO: 8;

a forward primer of PVX-FsPLΔSP has a nucleotide sequence set forth in SEQ ID NO: 9;

a reverse primer of PVX-FsPLΔSP has a nucleotide sequence set forth in SEQ ID NO: 8;

a forward primer of pCAMBIA2300-FsPL has a nucleotide sequence set forth in SEQ ID NO: 14;

a reverse primer of pCAMBIA2300-FsPL has a nucleotide sequence set forth in SEQ ID NO: 15;

a forward primer of pCAMBIA2300-FsPLΔSP has a nucleotide sequence set forth in SEQ ID NO: 16;

a reverse primer of pCAMBIA2300-FsPLΔSP has a nucleotide sequence set forth in SEQ ID NO: 15.

The present invention further provides use of the FsPL gene, the protein, the silencing vector and the silent recombinant bacterium in manufacturing a peptide medicament against sugarcane pokkah boeng fungi, in particular to use of the gene sequence, the protein, and the like to develop related anti-disease fungus peptide medicaments.

The technical schemes provided by the present invention will be described in detail below with reference to the examples, which, however, should not be construed as limiting the scope of the present invention.

Test Example 1

1 Materials and Methods

1.1 Experimental Materials

Test plants: the test sugarcane cultivar was “Zhongzhe 1” cultivated by Guangxi University; this particular cultivar is susceptible to the pokkah boeng disease, and the photoperiod was 16 h:8 h (light:dark); the test tobacco (*Nicotiana benthamiana*) was cultivated in a greenhouse with a 16:8 (light:dark) photoperiod. Test strains: *E. coli* Top10 competence, purchased from Shanghai Weidi Biotech Co., Ltd.; Trans1-T1 competence, purchased from Beijing TransGen Biotech Co., Ltd., cultured in an LB medium at a constant temperature of 37° C.; *Agrobacterium* competence GV3101, purchased from Shanghai Weidi Biotech Co., Ltd.; the GV3101 strain contains the pJIC SA_Rep concomitant factor so normal replication of PVX plasmid can be ensured in *Agrobacterium* and the GV3101 strain is cultured in an LB medium at a constant temperature of 28° C.

Test vector: Potato Virus X (PVX), gifted by academician Zhensheng Kang from Northwest A&F University (Chunlei Tang. Identification and Functional Analysis of Effector Proteins and Genes Inducing Host Cell Necrosis in Interactions of *Puccinia striiformis* with Wheat [D]. Northwest A&F University, 2013;

Likun Wang, Xin Fan, Chunlei Tang, et al. Inhibition of Accumulation of Callose and Reactive Oxygen Species in Plants by *Puccinia striiformis* Effector Pst30 [J]. Acta Phytopathologica Sinica, 2020(2):9).

1.2 Experimental Methods 1.2.1 The conserved domain of the protein encoded by the gene of interest was predicted and analyzed using an online tool Conserved Domain Search (website: https://www.ncbi.nlm.nih.gov/). The signal peptide region of the protein was predicted and analyzed using online tools SignalP 4.1 (www.cbs.dtu.dk/services/SignalP/) and SMART (http://smart.embl-heidelberg.de/smart/set_mode.cgi?NORMAL=1). Primer design was performed using the Primer-BLAST (https://www.ncbi.nlm.nih.gov/tools/primer-blast/) tool; the qRT-PCR primer was designed using the IDT (https://www.ncbi.nlm.nih.gov/tools/primer-blast/) tool. Homology analysis was performed on the cloned target fragment by using BLAST alignment analysis software, and multi-sequence alignment analysis was performed by using DNAMAN software.

TABLE 1

Primer sequences

| Name of primer | Sequence information |
|---|---|
| PVX-GFP | F: AGCACCAGCTAGCATCGATATGAGTAAAGGAGAAGAACTTTTCA CTGG (set forth in SEQ ID NO: 3)<br>R: ATCGTATGGGTACGCGGCCGCTTTGTATAGTTCATCCATGCCATG TGTAATC (set forth in SEQ ID NO: 4) |
| PVX-BAX | F: AGCACCAGCTAGCATCGATATGGACGGGTCCGGGGA (set forth in SEQ ID NO: 5)<br>R: ATCGTATGGGTACGCGGCCGCGCCCATCTTCTTCCAGATGGTG (set forth in SEQ ID NO: 6) |
| PVX-FSPL | F: AGCACCAGCTAGCATCGATATGCACGCCTCCAGCCT (set forth in SEQ ID NO: 7)<br>R: ATCGTATGGGTACGCGGCCGCCTAGCACTTGCCAGCCTTGG (set forth in SEQ ID NO: 8) |
| PVX-FSPLΔSP | F: AGCACCAGCTAGCATCGATATGTGTCTCGGCTACACCGGC (set forth in SEQ ID NO: 9)<br>R: ATCGTATGGGTACGCGGCCGCCTAGCACTTGCCAGCCTTGG (the same as PVX-FSPL) (set forth in SEQ ID NO: 8) |

TABLE 1-continued

Primer sequences

| Name of primer | Sequence information |
|---|---|
| NB_EF-1 | F: TGGTGTCCTCAAGCCTGGTAT (set forth in SEQ ID NO: 10)<br>R: ACGCTTGAGATCCTTAACCGC (set forth in SEQ ID NO: 11) |
| PCAMBIA2300-BAX | F: AGGTCGACTCTAGAGGATCCATGGACGGGTCCGGGGA (set forth in SEQ ID NO: 12)<br>R: ACATACGCGTGGTACCGCCCATCTTCTTCCAGATGGTG (set forth in SEQ ID NO: 13) |
| PCAMBIA2300-FSPL | F: AGGTCGACTCTAGAGGATCCATGCACGCCTCCAGCCT (set forth in SEQ ID NO: 14)<br>R: ACATACGCGTGGTACCCTAGCACTTGCCAGCCTTGG (set forth in SEQ ID NO: 15) |
| PCAMBIA2300-FSPLΔSP | F: AGGTCGACTCTAGAGGATCCATGTGTCTCGGCTACACCGGC (set forth in SEQ ID NO: 16)<br>R: ACATACGCGTGGTACCCTAGCACTTGCCAGCCTTGG (the same as PCAMBIA2300-FSPL) (set forth in SEQ ID NO: 15) |
| FSPL-A | F: GACTGGCGAAATAACCAGATCGA (set forth in SEQ ID NO: 17)<br>R: ATGTTTGTATCGGCTTGATATTGCTC (set forth in SEQ ID NO: 18) |
| FSPL-B | F: TCTGGCGGTTGGGAGAGT (set forth in SEQ ID NO: 19)<br>R: CGAGGCATTCTTGGGTCATTTTAG (set forth in SEQ ID NO: 20) |
| HPH | F: CGGTACCCGGGGATCCTCTAG (set forth in SEQ ID NO: 21)<br>R: GCCTGCAGGTCGACAGAAGATG (set forth in SEQ ID NO: 22) |
| Detection primer 1 | FSPL-F1: GGAGCTTGGCGTTACCTGTC (set forth in SEQ ID NO: 23)<br>HPH-R1: GGGAGACGAGATCAAGCAGAT (set forth in SEQ ID NO: 24) |
| Detection primer 2 | HPH-F2: TCGCGCATATGAAATCACGC (set forth in SEQ ID NO: 25)<br>FSPL-R2: CCTCCCGCTCCAATAAGCAT (set forth in SEQ ID NO: 26) |

1.2.2 *Agrobacterium*-Mediated Transient Expression of the Gene in *Nicotiana benthamiana*

Transient expression of FsPL was performed in tobacco leaves to verify the function of the gene. Different fragments (FsPL-FL, FsPL-Δsp) of FsPL1 were amplified using the cDNA of the *F. sacchari* wild-type strain as a template and were inserted into the PVX vector at the ClaI and NotI sites, and the vector was transformed into *Agrobacterium* GV3101. *Agrobacterium* permeation tests were performed on tobacco leaves. Sites into which PVX empty vector and PVX-GFP were injected were used as negative controls, and a site into which PVX-Bax was inoculated was used as a positive control. After 7 d, the symptoms were observed and photographed, during which attention was paid to symptom changes, and each treatment was repeated at least 3 times. Gene expression was detected by qRT-PCR and Western blot.

1.2.3 Elicitation of PTI response in hosts by FsPL *Agrobacterium* carrying the gene of interest was injected into 4-6 week old *Nicotiana benthamiana* leaves. To study ROS accumulation, tobacco leaves that had been infected for 48 h were collected and stained with 1 mg/mL 3',3-diaminobenzidine (DAB), and chlorophyll in the leaves was removed with absolute ethanol. Reactive oxygen species deposition was observed and photographed. To measure the leakage of electrolytes in the tobacco leaves, 48 h after *Agrobacterium* infection, the leaves in the infection area are collected using a 1 cm diameter hole punch. The leaf punches were placed in sterile deionized water and kept for 2 h at a rotational speed of 165 rpm at a temperature of 25° C. The ionic conductivity was measured on FiveEasy FP30 (Mettler-Toledo, Shanghai). To observe callose deposition, leaves that had been infected for 48 h were stained with 0.1% aniline blue, and callose deposition was observed under a fluorescence microscope. All the experiments were performed three times in total.

1.2.4 Gene Gun-Mediated Transient Expression of the Gene in Maize Leaves to further analyze the function of the FsPL gene, overexpression of FsPL was performed by gene gun bombardment in the leaves of maize B73, which is a very close relative to the sugarcane host for *F. sacchari*. +1 position leaves of the 5-leaf-stage maize plants with the same growth pattern were cut into 6 cm long leaf segments, and the main veins were removed. The leaves were pasted in parallel on Petri dishes. The maize leaves were bombarded with Bio-Rad PDS-1000/He at a distance of 6 cm under a pressure of 1100 psi. The bombarded leaves were cultured in the dark at 28° C. for 2 d, stained with GUS staining solution and decolored in 100% ethanol, and then the blue spots were counted. The experiment was repeated 3 times.

1.2.5 Gene Knock-Out Mutant Construction To obtain a mutant strain in which the FsPL gene is deleted, a homologous recombinant fragment comprising both flanks of the gene of interest and the hygromycin (Hph) gene sequence was constructed. Both flank sequences upstream and downstream of the FsPL gene were amplified from the genome DNA of the *F. sacchari* wild-type strain by using primers FsPL-AF/AR and BF/BR, respectively, about 1000 bp each. The two fragments were fused with the hygromycin gene by fusion PCR and the fused fragment (about 4200 bp) was transferred into *F. sacchari* protoplasts by PEG-mediated fungal genetic transformation. The transformed strains were screened for hygromycin resistance. The transformed strains with resistance were identified by PCR and purified by monospore isolation or protoplast regeneration.

1.2.6 Mutant Biophenotype and Pathogenicity Analysis (1) Colony morphology and growth rate determination: Bacterial cakes of the wild-type WT and mutant ΔFsPL were collected using a 6 mm diameter hole punch and each was transferred to a plate containing 15 mL of PDA medium. The cakes were cultured inverted at 28° C. in the dark for 7 days. The colony diameter was measured every 24 h, and the colony morphology was observed and recorded. Hypha growth curves were drawn based on the recorded data.

(2) Conidium count: The bacterial cakes (6 mm) of the test strains were each transferred to a CMC medium and cultured at 28° C. with shaking for 3 d, then conidium suspensions were obtained, and conidia were counted using a hemocytometer.

(3) In-vitro leaf inoculation to sugarcane: +1 position leaves of the 5-leaf-stage maize plants with the same growth pattern were selected and cut into 6 cm long leaf segments with disinfected scissors, and 2 cm cuts were made in the same positions on both sides of the leaf vein. The leaves were placed in Petri dishes (with filter paper wet with sterile water in them). Bacterial cakes of the wild-type strain and knock-out mutant strain that had grown in PDA media for 7 d were collected using a 6 mm diameter hole punch and inoculated to the cuts on Zhongzhe 1 leaves. After 3 d of incubation in the dark in a moist environment at 28° C., the formation of lesion spots on the leaves was observed and photographed. The inoculation experiment was repeated 3 times, 10 leaves inoculated each time.

(4) Cellophane penetration tests: Bacterial cakes of the wild-type strain (WT) and mutant strain (ΔFsPL) from the same batch of culture were collected using a 6 mm diameter hold punch and inoculated on PDA media covered in cellophane. Three replicates were set. After 3 d of inverted incubation in an incubator at a constant temperature of 28° C., photographic records of colony growth were made. The cellophane (containing hyphae) was removed from the surface of the media, placed back in the incubator and cultured for another 3 days. Whether colonies were able to grow on PDA media was observed and photographic records were made.

1.2.7 Determination of the Activity of Pectate Lyase Bacterial cakes of the wild type and mutant were collected using a hole punch, placed into 100 mL of culture media for pectate lyase and cultured at 28° C. with shaking at 210 rpm. After 5 d, their crude enzyme solutions after boiling inactivation were used as controls, the absorption of the crude enzyme solutions at the wavelength of 540 nm was measured by DNS colorimetric method, and the D-galacturonic acid content was calculated from the standard curve. At 50° C. at pH 4.8, 1 mL of pectinase decomposes pectin for 1 h to produce 1 mg of D-galacturonic acid as one enzymatic activity unit (U). Three replicates were set for the experiment, and the experiment was repeated 3 times.

2 Results and Analysis 2.1 Results of Sequence Analysis

FsPL ORF is 702 bp in full length, encodes 233 amino acids and has a signal peptide of 19 aa at the N terminus, and aa at positions 23 to 222 form the pectate lyase domain of the gene (FIG. 1: the FsPL gene has a pectate lyase domain).

2.2 FsPL can Induce Tobacco Cell Necrosis

The activity of the gene of interest to induce cell necrosis was measured through its transient expression in *Nicotiana benthamiana* leaves. The results are shown in A of FIGS. 2A-2C. Significant cell death can be seen at the site where Bax was injected, indicating that Bax was successfully expressed in the system and induced host cell necrosis. In the present invention, cell necrosis was observed at neither the site where the empty vector (EV) was injected nor the site where GFP was injected as a negative control. Cell necrosis can be seen at the site where FsPL was injected. After decoloring with absolute ethanol, cell necrosis was more notable on the leaves; this is consistent with the result for the positive control, indicating that the gene induced programmed cell death (PCD) of host cells. After the signal peptide was removed from the FsPL gene, a vector was constructed and transiently expressed in *Nicotiana benthamiana*. The results show that the gene with the signal peptide deleted induced necrosis to a significantly reduced degree. The RT-PCR results show that the gene was successfully transcribed (in FIG. 2B), and the Western blot results show that the protein was successfully expressed (in FIG. 2C).

FIGS. 2A-2C: the FsPL gene can elicit PCD response in *Nicotiana benthamiana*. As a positive control, Bax can induce cell death in tobacco leaves. FaPL can induce cell death in tobacco leaves; this is consistent with the result for the positive control. After the deletion of the signal peptide, the degree of necrosis was reduced (in FIG. 2A). Two days after infection, tobacco leaves were collected and RNA was extracted from them. With NbEF-1 as an internal reference, the RT-PCR results show that the gene was successfully transcribed (in FIG. 2B), and the Western blot results show that the protein was successfully expressed (in FIG. 2C).

2.3 FsPL Triggers PTI Response

One of the immune responses plants produce against invasions of pathogens is the production of a large amount of reactive oxygen species (ROS). The present invention used DAB for staining, and the results show that the sites where GFP and PVX were injected could not be stained brown, serving as a negative control; the site where Bax was injected was stained brown, serving as a positive control. At the site infected with FsPL, significant brown deposits can be seen; this is consistent with the positive control, indicating that FsPL caused a burst of reactive oxygen species in *Nicotiana benthamiana* leaf tissue. After the deletion of the signal peptide, the site was less brown, indicating that the ability of FsPL to cause a burst of reactive oxygen species was reduced (in FIG. 3A). The occurrence of PTI response in plants is often accompanied by electrolyte leakage. Therefore, the change in conductivity caused by plant cell electrolyte leakage was measured in the present invention. The results show a very significant increase in conductivity of the FsPL-infiltrated area compared to the negative control (the site where GFP was injected). After the deletion of the signal peptide, electrolyte leakage decreased to some extent (in FIG. 3B). Callose accumulation is a common physical protective barrier in the innate immune responses of plants. After pathogens invade, plants block sieve pores by secreting a large amount of callose, thereby preventing the pathogens from moving in cells.

After staining with aniline blue, callose deposited on the cell wall can be stained blue and is visible under a fluorescence microscope. In the present invention, callose accumulation caused after tobacco leaves were infected with FsPL was detected using aniline blue. The results show that compared to the negative control GFP, the infiltration areas of the positive control Bax and FsPL presented large areas of blue fluorescence. After the deletion of the signal peptide, callose deposition decreased to some extent (in FIG. 3C). The above results show that FsPL triggered PTI response in plants and the signal peptide played some role.

Figure 3C:
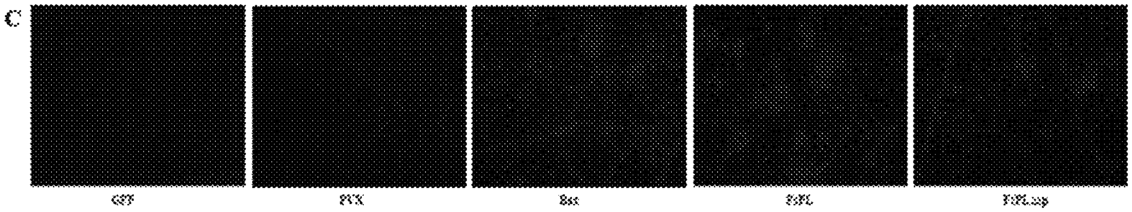

FIGS. 3A-3C: FsPL elicits PTI response in *Nicotiana benthamiana*. DAB staining detects a burst of reactive oxygen species caused by transient expression of the gene in *Nicotiana benthamiana* (in FIG. 3A); electrolyte leakage caused by the gene (in FIG. 3B), where error bars indicate the standard errors for 3 biological repeats and technical repeats, ns indicates no significant difference ($P>0.05$), * indicates a significant difference ($P<0.05$), and  and * indicate very significant differences ($P<0.01$); observation of callose deposition through aniline blue staining (FIG. 3C).

2.4 Transient Expression of the FsPL Gene Leads to Induction of Cell Necrosis in Maize Leaves To further verify the function of the FsPL gene, maize leaves were bombarded with a gene gun, and overexpression of the FsPL gene was performed in the leaves of maize, which is a very close relative to sugarcane (the host for *F. sacchari*). The results of gene gun bombardment show that many blue spots appeared on the leaves bombarded with GUS+EV, indicating that the gene gun-mediated transient expression in the maize leaves was successful, serving as a negative control. The number of blue spots on the leaves bombarded with GUS+Bax decreased by about 88.36%; Bax can elicit PCD response in plants, serving as a positive control. The number of blue spots on the leaves bombarded with GUS+FsPL decreased by about 76.72%, indicating that FsPL can induce cell necrosis in maize leaves. The number of blue spots on the leaves bombarded with GUS+FsPLΔsp decreased by about 51.64%, indicating that after removal of the signal peptide, the gene could still elicit PCD response, but its ability to induce PCD decreased to some extent (FIG. 4).

FIG. 4: FsPL elicits PCD response in maize leaves. Note: a. the DNA content was the same in barrel 1 and barrel 2, and all the repetitions were performed on maize leaves with the same growth pattern; EV: empty vector; b. the ratio values of blue spots in barrel 1 to barrel 2 represent mean±standard deviation; c. $P<0.05$ indicates a significant difference, and $P<0.01$ indicates a very significant difference.

2.5 FsPL is a Virulence Factor for *F. sacchari*

To investigate the function of the FsPL gene in *F. sacchari*, the FsPL gene in the *F. sacchari* strain was knocked out by homologous recombination, yielding a mutant strain ΔFsPL. The mutant strain was thinner than the wild-type colonies, and produced significantly fewer aerial hyphae (FIG. 8) and had a slightly slower hyphal growth rate (FIG. 9). However, the sporulation quantity of the mutant did not significantly change (FIG. 10). In the present invention, the pathogenicity of the wild type and mutant was determined: an in-vitro inoculation experiment was conducted on sugarcane leaves (FIG. 12). The results show that the ΔFsPL mutant demonstrated a significantly smaller area of necrosis on sugarcane leaves in the infected area than the wild type (FIG. 13). This indicates that the deletion of the FsPL gene caused a decrease in the pathogenicity of the *F. sacchari* strain. Given that the pathogenicity of plant pathogenic fungi is generally related to their ability to penetrate the epidermis of the host, to gain insight into whether deletion of the FsPL gene affects the ability of hyphae to invade, cellophane penetration experiments were conducted. The results show that the ΔFsPL knock-out mutant was unable to penetrate cellophane—the ability to penetrate decreased (FIG. 11). Therefore, the present invention speculates that the FsPL gene affects pathogenicity by affecting the ability of *F. sacchari* hyphae to penetrate.

FIGS. 5-13: mutant phenotype and pathogenicity determination; a gene knockout strategy and relative positions of the primers (FIG. 5); three pairs of primers (Hph-F/R, FsPL-F1+Hph-R1, Hph-F2+FsPL-R2) detects positive transformants (FIG. 6); MluI digestion verification; the FsPL gene comprises a digestion site for the enzyme MluI and thus can be digested by MluI, and digestion results in two bands; Hph does not comprise a digestion site for the enzyme MluI and thus cannot be digested by MluI (FIG. 7); the phenotype of the mutant and wild-type strains in PDA media (FIG. 8); the growth curves of the mutant and wild type (FIG. 9); the number of conidia of the mutant and wild type, where ns indicates no significant difference ($P>0.05$) (FIG. 10); cellophane penetration experiments (FIG. 11); in-vitro inoculation of sugarcane leaves (FIG. 12); statistics on the area of necrosis in sugarcane leaves, where * indicates a significant difference ($P<0.05$) (FIG. 13).

2.6 Deletion of the FsPL Gene Affects the Extracellular Pectinase Activity of *F. sacchari*

A standard curve was drawn for D-galacturonic acid, and the regression equation yielded was $y=1.5617x-0.0182$, $R2=0.997$ (in FIG. 14A). The extracellular pectinase activity of the mutant and wild type was obtained according to the regression equation. The results show that the extracellular pectinase activity of *F. sacchari* significantly decreased after the deletion of the FsPL gene from it (in FIG. 14B). This indicates that deletion of the FsPL gene affected the extracellular pectinase activity of *F. sacchari*.

FIGS. 14A-14B: an assay for the activity of pectate lyase; the D-galacturonic acid standard curve (in FIG. 14A); the assay for the extracellular pectate lyase activity of the mutant and wide type, where ** indicates a very significant difference ($P<0.01$) (in FIG. 14B).

3 Conclusion and Discussion

Pectin is the most complex and dominant component of the plant cell wall. Pathogenic bacteria have to break through this barrier when invading plants. Pectate lyase is an important cell wall-degrading enzyme, which can help pathogens to successfully invade and colonize host plants and expand. Pectate lyase is widely sourced and usually exists in multigene family form. In 1989, a pectate lyase gene was reported to be found in *Aspergillus nidulans*. After that, pectate lyase genes were also found in pathogens such as *Colletotrichum gloeosporioides, Nectria hematococca, Trichoderma viride, Aspergillus niger, Alternaria brassicicola, Phytophthora capsici, Verticillium dahliae*. The present invention reports the pectate lyase gene FsPL in *F. sacchari*. The *Agrobacterium*-mediated transient expression in tobacco leaves and gene gun-mediated transient expression in maize leaves indicates that FsPL can elicit PCD response in *Nicotiana benthamiana* and maize leaves. The pectate lyase genes in pathogens can cause damage to the cell walls of their host plants by degrading pectin, the major component in the cell walls, and finally cause cell death. FsPL has a signal peptide at the N terminus. When the signal peptide was deleted from FsPL, the PCD response elicited by the gene in plants was found to be weakened, which indicates that the signal peptide played some role in the functioning of the gene. Since signal peptides are an important component of secretory proteins, the deletion of the signal peptide may affect the recognition of proteins by plants; this requires further experimental investigations.

PTI, as a nonspecific defense response in plants, resists invasions of pathogens through a series of physiological reactions such as bursts of reactive oxygen species, electrolyte leakage and callose accumulation. According to the present invention, the measurement of these physiological indicators indicates that FPL could elicit typical PTI response in plants and the signal peptide played some role in this process. Previous studies show that the pectate lyase family members can elicit immune responses in hosts; for example, the pectate lyase gene MoPL1 of *Magnaporthe grisea* can serve as a DAMP to elicit PTI response in tobacco leaves, and both the pectate lyase gene VdPEL1 of *Verticillium dahliae* and the pectate lyase gene BcSpl1 of *Botrytis cinerea* can elicit immune defense responses in plants. It was speculated from these results that FsPL can not only be used as a pectate lyase to directly participate in degrading plant cell walls but also be used as a DAMP to elicit PTI response in plants.

In the present invention, a knock-out mutant of *F. sacchari* was constructed by knocking out the FsPL gene, and the results indicate that the knock-out mutant produced significantly fewer aerial hyphae and had a slightly slower hyphal growth rate while the spore morphology and sporulation quantity did not significantly change, which indicates that the gene may play a role in the vegetative growth of pathogens but not in the regulation of sporulation. In-vitro inoculation experiments show that the pathogenicity of the mutant strain significantly decreased. In terms of the relationship between the pectate lyase gene and the pathogenicity of pathogens, the deletion of the pectate lyase gene may cause a decrease in the pathogenicity of the pathogens on plants.

To further analyze the mechanism of the FsPL gene affecting the pathogenicity of pathogens, the present invention tested the ability of mutant hyphae to penetrate through cellophane penetration experiments, and the results show that the mutant ΔFsPL could not penetrate cellophane—the ability to penetrate decreased. Therefore, it was speculated that the deletion of the FsPL gene affected the ability of *F. sacchari* hyphae to penetrate. The pectinase secreted by pathogens participates in a pathogenic process by degrading the pectin of plant cell walls. The present invention measured the extracellular pectate lyase activity by the DNS method, and the results show that the extracellular enzymatic activity of the mutant significantly decreased. In conclusion, the FsPL gene affects the degradation of plant cell walls by affecting the extracellular enzymatic activity of *F. sacchari*, further affects bacterial invasion and colonization, and finally affects the pathogenicity of pathogens.

The above descriptions are only preferred embodiments of the present invention. It should be noted that those of ordinary skill in the art can also make several improvements and modifications without departing from the principle of the present invention, and such improvements and modifications shall fall within the protection scope of the present invention. See the attached sequence listing for details.

What is claimed is:

1. A virulence factor FsPL gene from a sugarcane pokkah boeng disease, wherein the virulence factor FsPL gene from the sugarcane pokkah boeng disease has a sequence set forth in SEQ ID NO: 1.

* * * * *